US012207685B2

(12) United States Patent
Perrins et al.

(10) Patent No.: US 12,207,685 B2
(45) Date of Patent: Jan. 28, 2025

(54) VAPORIZING ARTICLE AND CONTAINERS FOR VAPORIZING ARTICLES

(71) Applicants: Rob Perrins, Ottawa (CA); Michel Bouchard, Ottawa (CA); Jean-Pierre Bouchard, Ottawa (CA)

(72) Inventors: Rob Perrins, Ottawa (CA); Michel Bouchard, Ottawa (CA); Jean-Pierre Bouchard, Ottawa (CA)

( * ) Notice: Subject to any disclaimer, the term of this patent is extended or adjusted under 35 U.S.C. 154(b) by 847 days.

(21) Appl. No.: 17/045,081

(22) PCT Filed: Apr. 3, 2019

(86) PCT No.: PCT/CA2019/050407
§ 371 (c)(1),
(2) Date: Oct. 2, 2020

(87) PCT Pub. No.: WO2019/191840
PCT Pub. Date: Oct. 10, 2019

(65) Prior Publication Data
US 2021/0145063 A1  May 20, 2021

(30) Foreign Application Priority Data
Apr. 3, 2018 (CA) .................................. CA 3000076

(51) Int. Cl.
| | | |
|---|---|---|
| *A24F 40/46* | (2020.01) | |
| *A24D 3/17* | (2020.01) | |
| *A24F 7/00* | (2006.01) | |
| *A24F 13/00* | (2006.01) | |
| *A24F 40/20* | (2020.01) | |
| *A24F 40/42* | (2020.01) | |
| *A24F 40/485* | (2020.01) | |
| *A61M 11/04* | (2006.01) | |
| *A61M 15/00* | (2006.01) | |

(52) U.S. Cl.
CPC ................ *A24F 40/46* (2020.01); *A24F 7/00* (2013.01); *A24F 13/00* (2013.01); *A24F 40/42* (2020.01); *A24F 40/485* (2020.01); *A61M 11/041* (2013.01); *A61M 15/0021* (2014.02); *A24D 3/17* (2020.01); *A24F 40/20* (2020.01)

(58) Field of Classification Search
CPC ... A24D 3/17; A24F 7/00; A24F 13/00; A24F 40/20; A24F 40/42; A24F 40/46; A24F 40/485; A61M 11/041; A61M 15/0021
See application file for complete search history.

(56) References Cited

U.S. PATENT DOCUMENTS

| | | | | |
|---|---|---|---|---|
| 9,167,849 B2* | 10/2015 | Adamic | ................... | A24F 13/06 |
| 10,555,552 B2* | 2/2020 | Batista | .................... | A61L 9/037 |
| 2015/0342259 A1* | 12/2015 | Baker | .................. | A24F 40/485 |
| | | | | 131/329 |
| 2017/0086504 A1* | 3/2017 | Cameron | ................ | A24F 40/48 |

* cited by examiner

*Primary Examiner* — Vanessa Girardi

(57) ABSTRACT

Systems and methods related to the near elimination of second-hand smoke or vapour from the process of smoking or vaporizing tobacco or *Cannabis* are provided. A vaporizing article is provided whereby a user may exhale into the article to capture a high percentage of the smoke and contaminants before they are released back into the surroundings. The article also provides for filtering gaseous by-products when the article is in idle mode. A prepackaged container for use with a vaporizing article is also provided. The container may be configured so as to optimize the heat distribution and consumption of product within the container.

4 Claims, 20 Drawing Sheets

VAPORIZING ARTICLE AND CONTAINERS FOR VAPORIZING ARTICLES

FIELD

This disclosure relates generally to articles for vaporizing a substance for inhalation by a user, and specifically to vaporizing articles and complementary products that allow a near-zero emission user experience.

BACKGROUND

Tobacco and *Cannabis* related products are typically burnt or vaporized to create smoke or vapour, which may be inhaled by the user. This may be done to create a certain euphoria- or medicinal-related purposes, but the combustion products can also represent a health risk. Generally, this risk is deemed acceptable by the user (the smoker). However, the burning or vaporization and exhalation of tobacco or *Cannabis* smoke or vapour by the user generates "second-hand smoke" which can also represent a health hazard to non-users, who do not necessarily accept that risk or are too young to understand or address that risk. Many countries now have strict laws related to where an individual is permitted to smoke, to address the risks of second-hand smoke to non-smokers. Some non-smokers are also allergic to smoke, which adds to the risk factor.

There are several additional negative consequences from the combustion and/or vaporization of tobacco and *Cannabis*. For example, smoke from tobacco and *Cannabis* can damage the interiors of rooms and automobiles leaving a pungent odour behind, which can be difficult and expensive to remove. One Ontario, Canada reference indicated that the cost to properly clean a rental apartment was in the order of $5000-$6000, to properly remove smoke-related odours.

Another negative consequence from the combustion or vaporization of tobacco and *Cannabis* is that smoke from tobacco and *Cannabis* can leave the clothes of the smoker with a lasting and unpleasant odour. Although this odour can often be washed out with a laundry process, it leaves the smoker with a potentially socially unacceptable smell until they change their clothes. This may be a more significant issue with *Cannabis* smokers, due to its more pungent odour.

As Canada prepares for the legalization of *Cannabis*, there are many ongoing debates as to where it should be allowed. Many of the latest discussions are related to trying to have it banned from rental properties, particularly apartment dwellings where it not only affects the apartment interior, but adjacent occupants' enjoyment of their living space as well, since the smoke can drift between balconies, down hallways and through ventilation systems, since rental apartments are not hermetically sealed.

In recent years the use of vaporizers to smoke tobacco and *Cannabis* have become more popular, since they represent a healthier solution to combustion. Although not completely free of health risks, vaporizers tend to be significantly better than the burning process since it can eliminate many of the toxins specific to the combustion process. Vaporizers represent a process more akin to boiling than to burning and as a result avoid some of the toxic by-products associated with actual combustion.

Table top and stand-alone filter systems do exist to reduce smoke in a room. However, their efficiency is limited by what air/smoke etc. passes through those systems. Their limitation is related to the fact that they cannot easily filter 100% of the room's air volume. They also cannot remove odours from porous surfaces which have already come in contact with the second-hand smoke, since it has already imbedded itself within those substrates.

External handheld filtration devices have been put forward in an attempt to better reduce the risks of second-hand smoke, but they add the inconvenience to the user of having to carry around and use a second device to exhale into, when enjoying the effects of tobacco or *Cannabis*.

The prior art lacks a device that provides an overall improved user experience, which includes burn optimization, improved euphoria and/or medicinal effect, second-hand smoke containment, ease of clean-up and overall simplicity of use.

SUMMARY

A first aspect of the present disclosure is associated to systems and methods related to the near elimination of second-hand smoke or vapour from the process of smoking or vaporizing tobacco or *Cannabis*. A mechanism uses a process where the user both inhales and exhales into a device. The device then filters out a high percentage of the smoke and contaminants, before it is released back into the surroundings. In one implementation uses P100 type filtering which is combined with activated charcoal filtering to eliminate an extremely high percentage of contaminants and odours associated with second-hand smoke. The device also contains the vaporization or burning process within the device in such a way that it filters the by-products while the device is idle between inhalations.

Another aspect of the present disclosure is associated with a vaporizing article comprising a heating chamber for receiving a substance to be heated, a heating means for inducing a gaseous by-product from the substance, a mouthpiece to allow inhalation of the gaseous by-product by a user and accept exhaled air from the user, and a filtering means for decontaminating the exhaled air prior to its dissipation back into the surroundings.

The vaporizing article may comprise a manifold for allowing flow of gaseous by-product from the heated substance toward the user's lungs as well as flow of exhaled air through the filtering means and out of the vaporizing article. The manifold may comprise a manifold inlet valve and a manifold outlet valve, wherein inhalation by the user causes the manifold inlet valve to open and the manifold outlet valve to close, and exhalation by the user causes the manifold outlet valve to open and the manifold inlet valve to close.

The vaporizing article may comprise a vapour regulator operatable to mix air with the gaseous by-product for inhalation. A predetermined mixture of gaseous by-product and air may be produced using a concentration control mechanism.

The vaporizing article may comprise a heating chamber located upstream from a cooling chamber, and a bypass conduit for allowing pressurized gaseous by-product to flow from the heating chamber into the filtering means.

The vaporizing article may comprise cooling means for extracting heat from gaseous by-product following toward the user's lungs and the cooling means may comprise a cooling tower with fins for providing increase surface area for contact with the gaseous by-products.

The vaporizing article may comprise a heat chamber door to permit selective access to the heat chamber to facilitate the introduction of substance into the heating chamber. The heat chamber door may comprise an air passageway to allow air outside of the vaporizing article to be drawn into the heating chamber. The heat chamber door may comprise protrusions configured to pierce a sealed container of substance inside the heating chamber when the heating chamber door is closed.

Another aspect of the present disclosure is associated with the use of a prepackaged container with a vaporizing article. The container may be configured so as to optimize the heat distribution and consumption of product within the container.

The container for holding a substance which when heated produces a gaseous by-product for inhalation by a user of the vaporizing article comprises a substantially cylindrical shaped exterior body and a central core. The body spans a first end and a second end of the container and the second end is substantially nozzle-shaped. The central core positioned within the body and extending from the first end of the container toward the second end of the container. The central core may is void of substance. Heat applied to the container causes heat to be transferred to the substance by walls of both the exterior body and the central core.

The container may comprise an airtight perforable sealing enclosure at the first end and a removable cap at the second end.

The container may comprise one or more thermally conductive spokes connecting the exterior wall to the central core.

BRIEF DESCRIPTION OF THE DRAWINGS

The following figures serve to illustrate various embodiments of features of the disclosure. These figures, which are illustrative and are not intended to be limiting, include.

DETAILED DESCRIPTION

It is to be understood that although the term "vaporizing article" is being used, the articles contemplated and described in this disclosure may alternatively utilize a combustion process to produce gaseous by-products from a substance such as tobacco, *Cannabis*, herbs, oils or the like.

FIGS. 1A, 1B, 1C, 1D and 1E show an exemplary embodiment of a vaporizing article 1 according to the present disclosure. The various inner components of the vaporizing article are contained within an outer casing 5. In this embodiment, the outer casing of the device is adapted to resemble and be similar in size to a common drinking flask, which offers the user an aesthetically-pleasing design that fits conveniently and comfortably into the user's pocket. It will be appreciated by those skilled in the art that the outer casing 5 may be adapted to any number of different shapes, provided the inside space defined by the outer casing is large enough to house the requisite inner components of the vaporizing article. The outer shell may be adapted to allow visual exposure of one or more inner components of the vaporizing article. For example, the outer shell may be provided with a viewing window 10 made of glass, transparent plastic or the like.

Figure 1A:
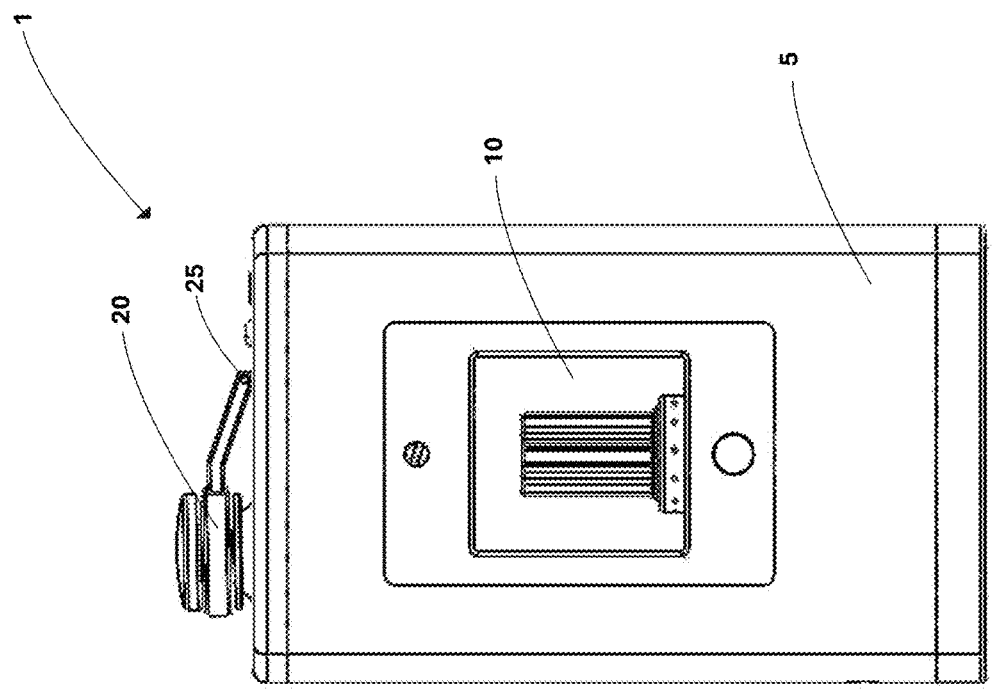
FIG. 1A, which is a front plane view of a vaporizing article according to an embodiment of the present disclosure.
Figure 1B:
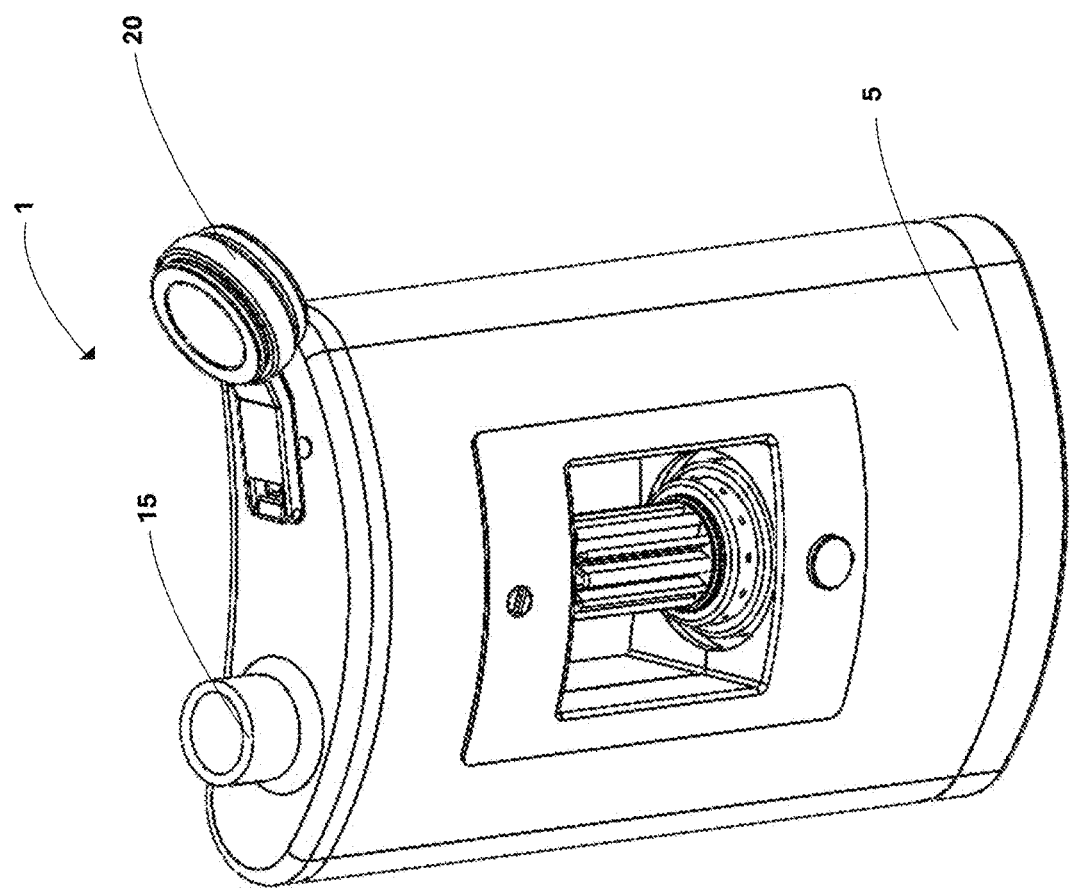
FIG. 1B, which is a perspective view of the vaporizing article of FIG. 1A.
Figure 1C:
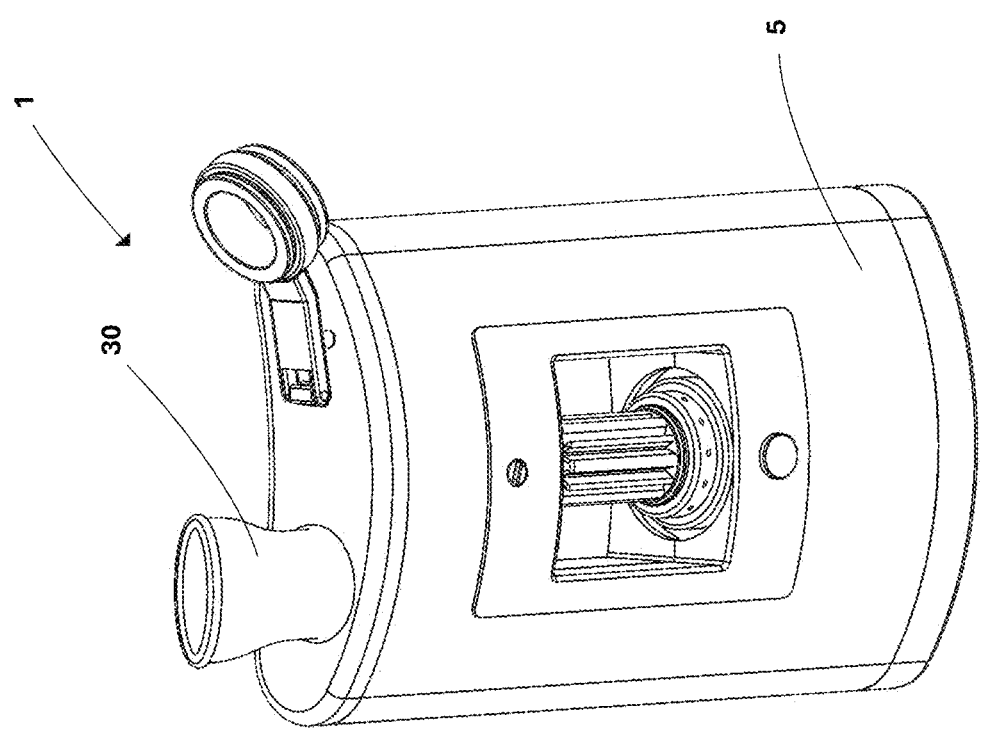
FIG. 1C, which is a perspective view of the vaporizing article of FIG. 1A, having an exemplary optional mouth piece attachment.

Vaporizing article 1 is adapted to have a mouthpiece 15 to allow a user to both inhale from and exhale into the vaporizing article. Optionally, a mouthpiece cover 20 may be provided to cap the vaporizing article when not in use. The mouthpiece cover 20 may for example be secured to the body using a hinged connection 25, allowing a user of the vaporizing article to conveniently make use of the mouthpiece cover 20. FIG. 1A shows the vaporizing article with the mouthpiece cover engaged with the mouthpiece, whereas FIG. 1B shows the cover in the open position, providing the user access to the mouthpiece 15. The mouthpiece may be configured to mate with various attachments according to the users' preferences or needs. For example, FIG. 1C shows a personal mouthpiece connector 30 that may be used when multiple users are using the vaporizing article but do not wish to share the same mouth piece for health reasons. Another example of an attachment may be a mask, similar in configuration to an oxygen mask, that covers the entirety of the user's mouth and nose.

Figure 1D:
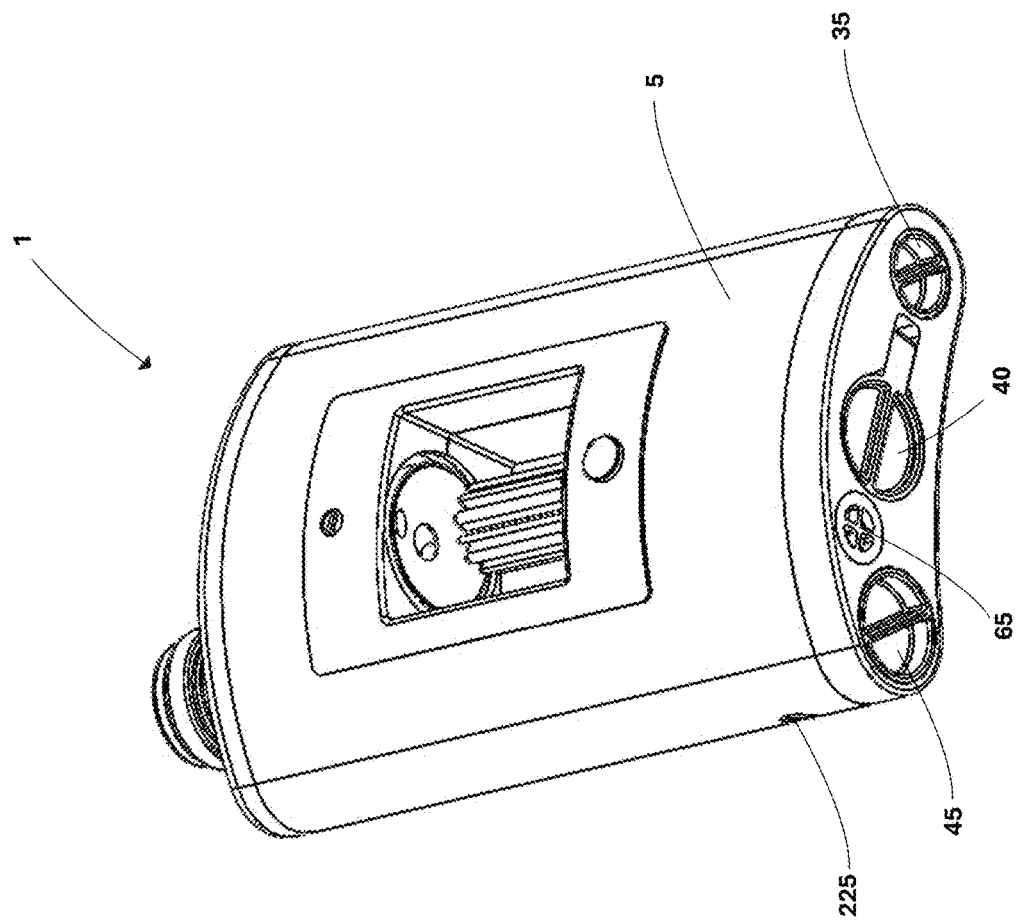
FIG. 1D, which is a perspective view of the vaporizing article of FIG. 1A.

Referring to FIG. 1D, the vaporizing article has a battery door 35, heat chamber door 40, and filter door 45 for giving the user selective access to a battery chamber 50, heat chamber 55 and filter chamber 60 (FIG. 3A), respectively. These doors 35, 40, 45 may be securable to the body of the vaporizing article, for example, by way of a threaded connection. The person of ordinary skill in the art would appreciate that any connection configuration that allows the user selective access to the chambers 50, 55, 60 would be suitable for the doors 35, 40, 45. The various chambers 50, 55, 60 are discussed in greater detail below. Vaporizing article 1 is also provided with one-way air inlet valve 65 which will also be discussed in greater detail below.

Figure 1E:
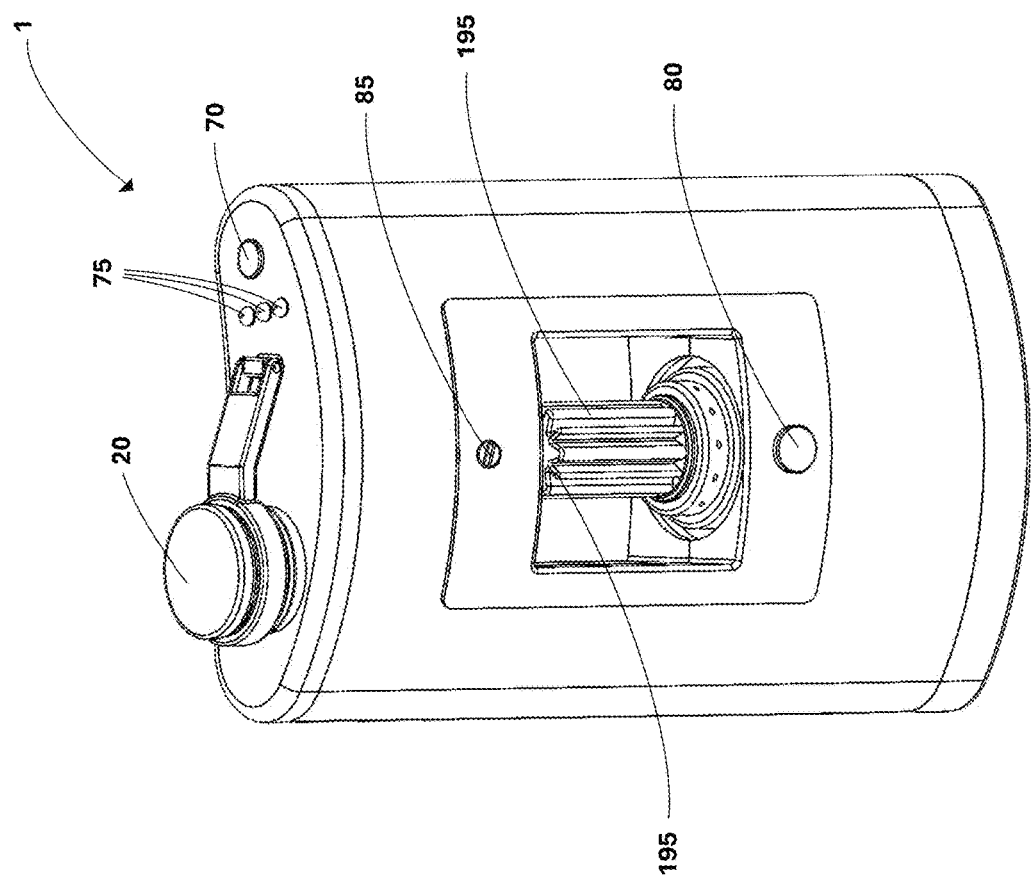
FIG. 1E, which is a perspective view of the vaporizing article of FIG. 1A.

With reference to FIG. 1E, the vaporizing article 1 may be provided with a power button 70 for turning the device on for use or off for preservation of battery and storage. One or more visual indicators, for example LEDs 75, may also be provided and visible from the outside of the body to prompt the user for any one of a number of reasons. For example, activation of one of the LEDs may signal to the user that the battery requires replacement or charging. Another LED may be used to notify the user when it is appropriate to inhale the vapour or smoke from the vaporizing article. The vaporizing article is also provided with an activation button 80 accessible to the user from the outside of the outer casing. As will be described in greater detail below, depression of the activation button 80 closes an airflow circuit to permit the user to inhale the desired smoke or vapour from the vaporizing article. A liquid fill port 85 may also be provided for allowing a user to change a liquid inside the cooling chamber (the cooling chamber and liquid that may contained therein are described in more detail below). The liquid fill port 85 may, for example, be similar to a small screw or a plastic cap that may be pushed and held in place similar to typical water pistol.

Figure 2:
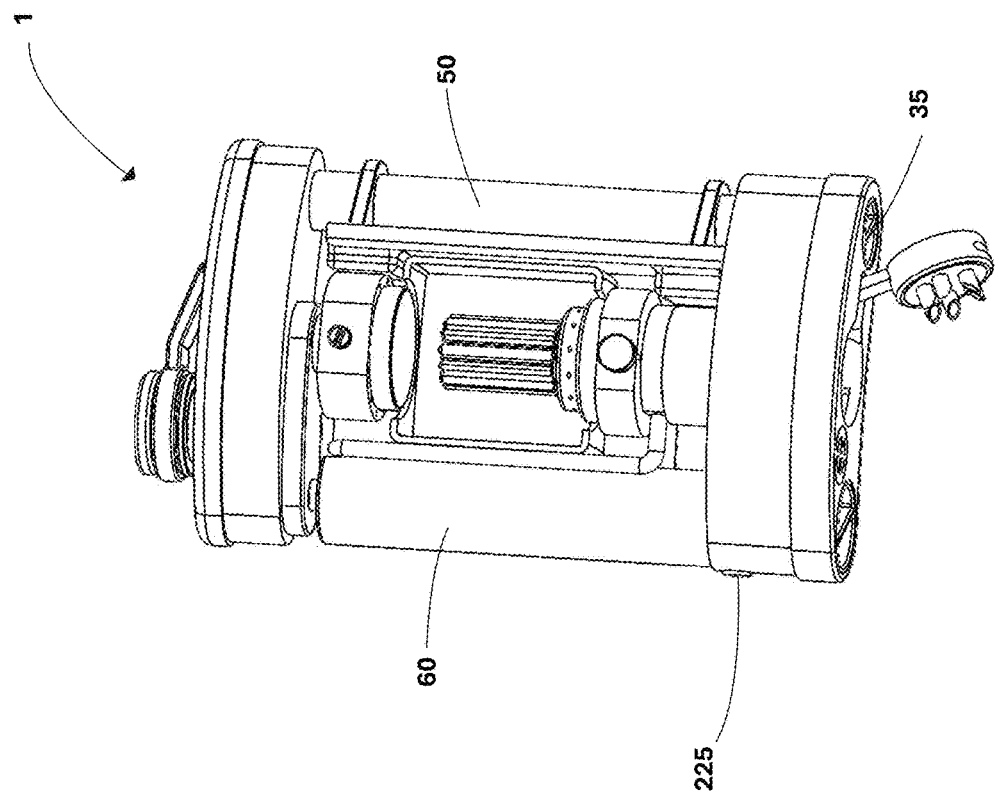
FIG. 2, which is a perspective view of the vaporizing article of FIG. 1A, with the outer casing and window frames omitted.

FIG. 2 shows the vaporizing article of FIGS. 1A through 1E with the outer casing and window frames removed. The vaporizing article 1 is provided with a battery chamber 50 and a filter chamber 60. The battery chamber 50 houses one or more auxiliary batteries (not shown) which provide power to the vaporizing article. The batteries may, for example, be standard alkaline batteries (AA or AAA) and can be conveniently removed and replaced by the user by virtue of the battery door 35. Alternative battery types, including rechargeable, may also be used to power the vaporizing article. The filter chamber 60 houses an auxiliary filter 90 (FIG. 8A), which is used to filter out a high percentage of the smoke and/or vapour and contaminants from the user's exhaled substrate before being released back into the user's surroundings. P100 type filtering may be used and may be combined with activated charcoal and or other filtering to eliminate an extremely high percentage of contaminants and odours associated with second-hand smoke. The permitted flow paths of the smoke and vapours and other contaminants inhaled and exhaled through the vaporizing article will be described in greater detail below. Filter 90 may be conveniently removed and replaced by virtue of filter door 45.

With reference to FIGS. 3A, 3B, 4A, 4B, 4C, and 4D the vaporizing article is provided with a heat chamber 55 where the substance to be heated and/or combusted within the vaporizing article will be contained. The substance may, for example, be tobacco, marijuana, oil, or another herb or substance that when heated and/or combusted and inhaled, provides a euphoric effect to a user. The heat chamber 55 in the exemplary embodiment described herein is adapted to receive pre-packaged container 95 (FIG. 4A) containing the substance. The use of pre-packaged containers would eliminate the need for the user to handle the substance (this includes having to grind and measure out specific quantities of the substance) and in some cases allow for a fresher product, since the product would be sealed until used. Pre-packaged containers would also provide for a quick and easy way to dispose of the used product after use. Pre-packaged containers may be fabricated according to known manufacturing techniques and may be made using various materials, including for example, plastic or metal. Preferably, most or all of the container would be made from sustainable materials.

It will be appreciated that the use of containers, although convenient, is not strictly required. Alternatively, the heat chamber 55 may accept loose particles of the substance, which would need to be removed and replaced by the user periodically, as the euphoric and/or medicinal effects of the substance are exhausted.

The container 95 may be shaped so as to optimize the efficacy of the heating and/or combustion of the substance in the container in order to maximize the euphoric experience extracted from a given amount of substance. For example, a container 95 such as that illustrated in FIGS. 4A and 4B may be used, which is generally cylindrical in shape at the inlet and throughout the majority of its length. At the outlet end 100, the container takes on a nozzle-like shape to concentrate the vapour and/or smoke as it exits from the container and further into the vaporizing article.

Figure 4A:
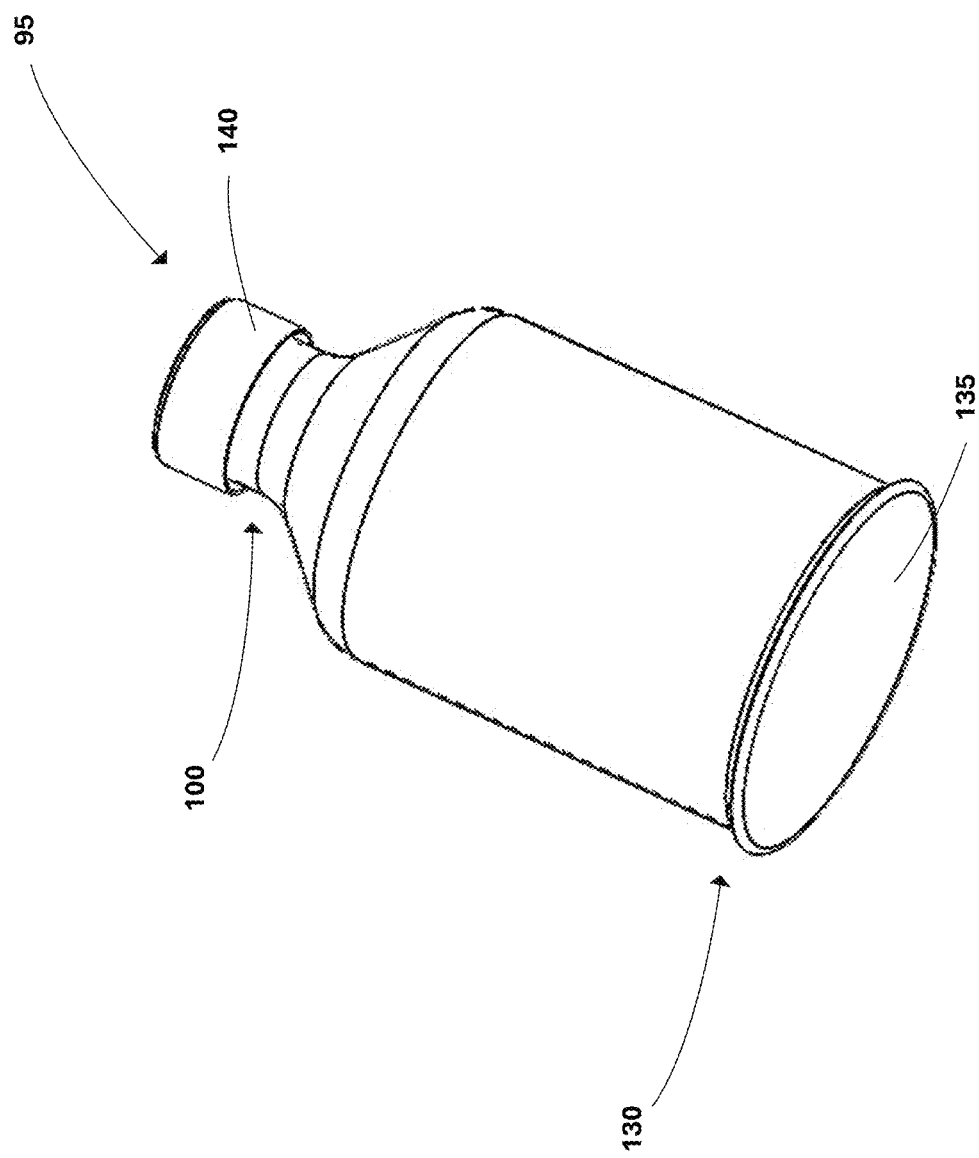
FIG. 4A, which is a perspective view of an exemplary container according to the present disclosure.
Figure 4B:
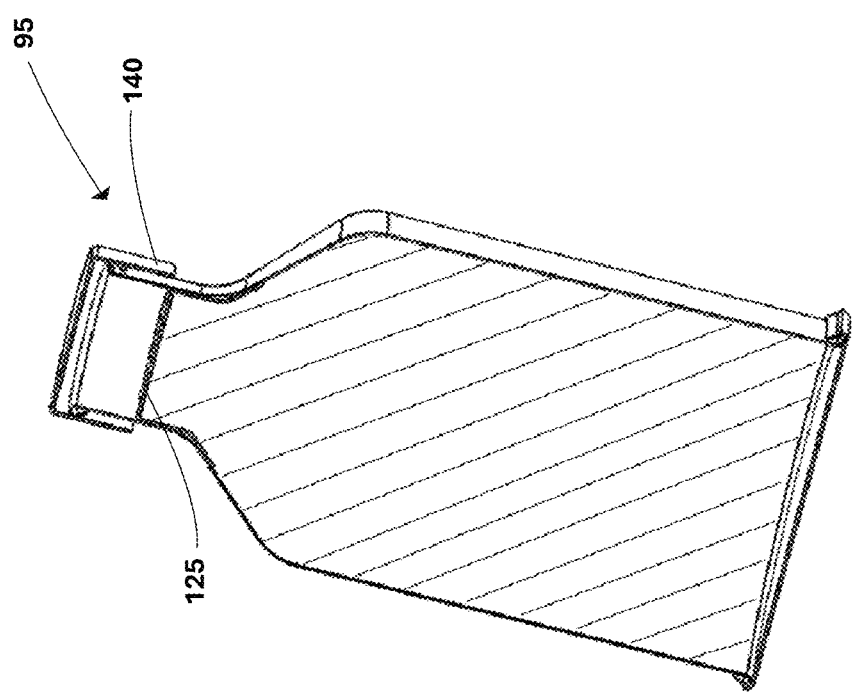
FIG. 4B, which is a cut-away view of the container of FIG. 4A
Figure 4C:
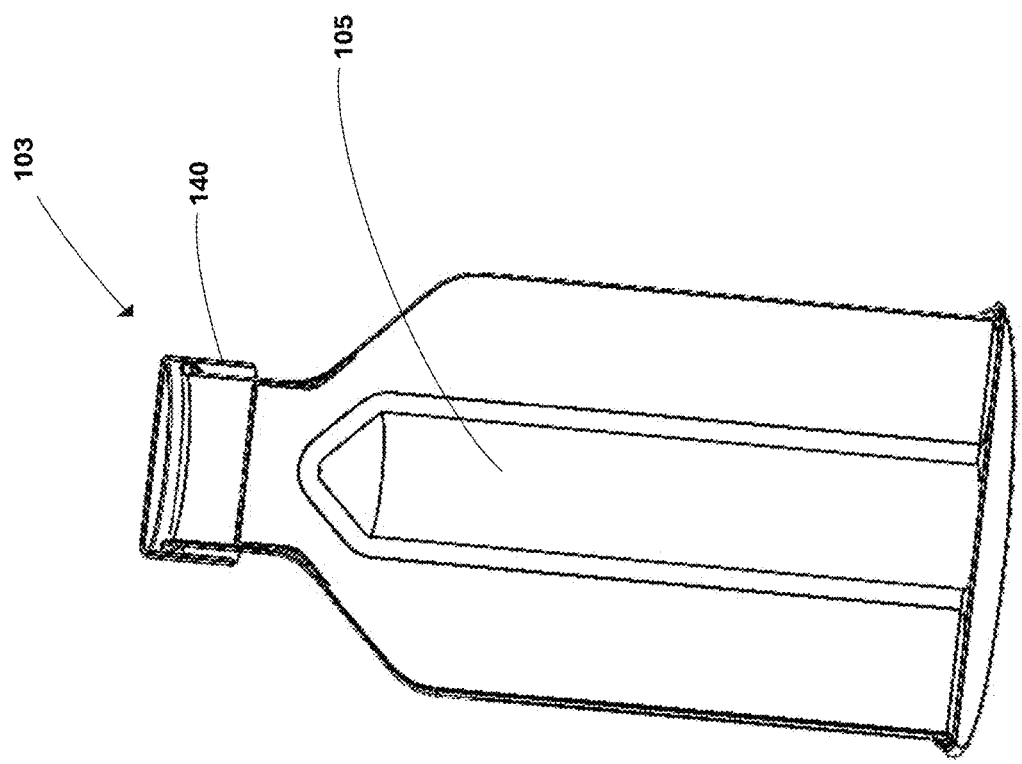
FIG. 4C, which is a perspective view of an alternative cored container according to the present disclosure.
Figure 4D:
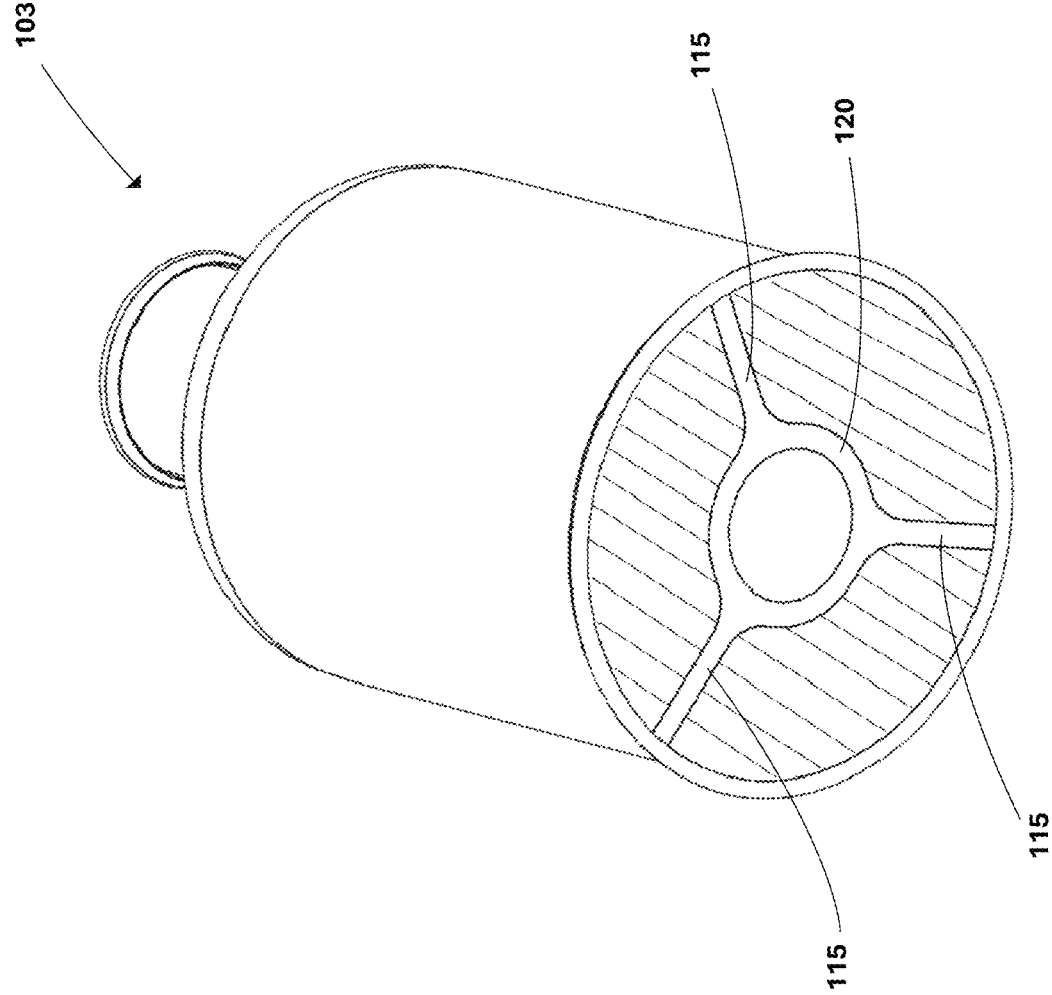
FIG. 4D, which is a perspective view of the container of FIG. 4C with the bottom seal omitted.

Optionally, an alternative container 103 may be provided with a centre core 105 generally shaped like a bullet, as shown in FIG. 4C. Although the core of the container illustrated in FIG. 4C is hollow, the core may alternatively be solid. The core acts as a barrier within the container and spaces the substance in an annular configuration. It will be appreciated that in the case of a vaporizing article using conduction heating, such annular spacing of the substance within the container leads to more evenly distributed heating of the substance and thus a more consistent and effective experience for the user. The attachment of the centre core 105 to the container 103 may be done in such a way that heat from the heating element 110 (FIG. 5A) may be conducted into the hollow centre core to provide secondary heating to the portion of the annulus of substance which is closest to the centre core. For example, with reference to FIG. 4D, spokes 115 running between the outer wall of the container and the centre core may be made from a suitably heat conductive material such that heat from the heating element 110 travels effectively through the spokes 115 to heat the wall 120 of the centre core and thus the substance adjacent the core within the container.

Container 95 or 103 may have an integrated filter 125 near the outlet end 100 to ensure that the loose substance inside the container does not infiltrate other portions of the vaporizing article. The filter may, for example, be a screen filter, and/or plastic filter similar to those commonly used in commonly-available filtered cigarettes. The inlet end 130 of the container may be provided with an airtight perforatable seal 135 to contain the substance inside the container and also preserve the freshness of the substance for as long as possible. The airtight seal may for example be a sheet made of foil pressed onto the sidewalls of the container. The seal may alternatively be made of any suitable material that is both substantially air-impervious and perforatable to allow air to be sucked through the container. The container may also be provided with a removable cap 140 at the outlet end 100. The cap 140 serves to seal the container 95 or 103 at the outlet end 100. The heating chamber 55 may be configured, for example through dimensional restrictions, such that it could not receive a container 95 or 103 unless the cap 140 has been removed.

Figure 3A:
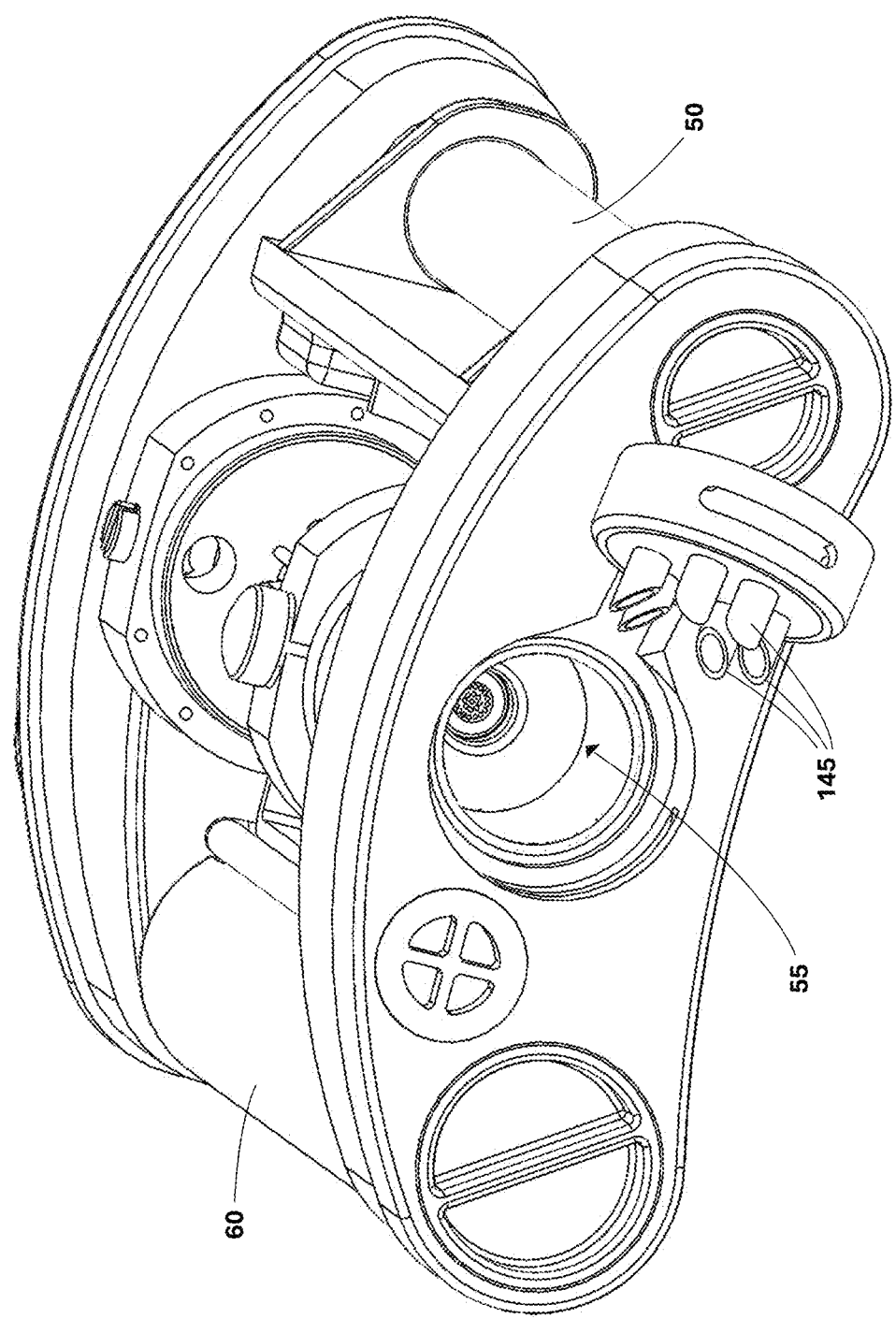
FIG. 3A, which is a perspective view of the vaporizing article of FIG. 1A, with the outer casing and window frames omitted.
Figure 3B:
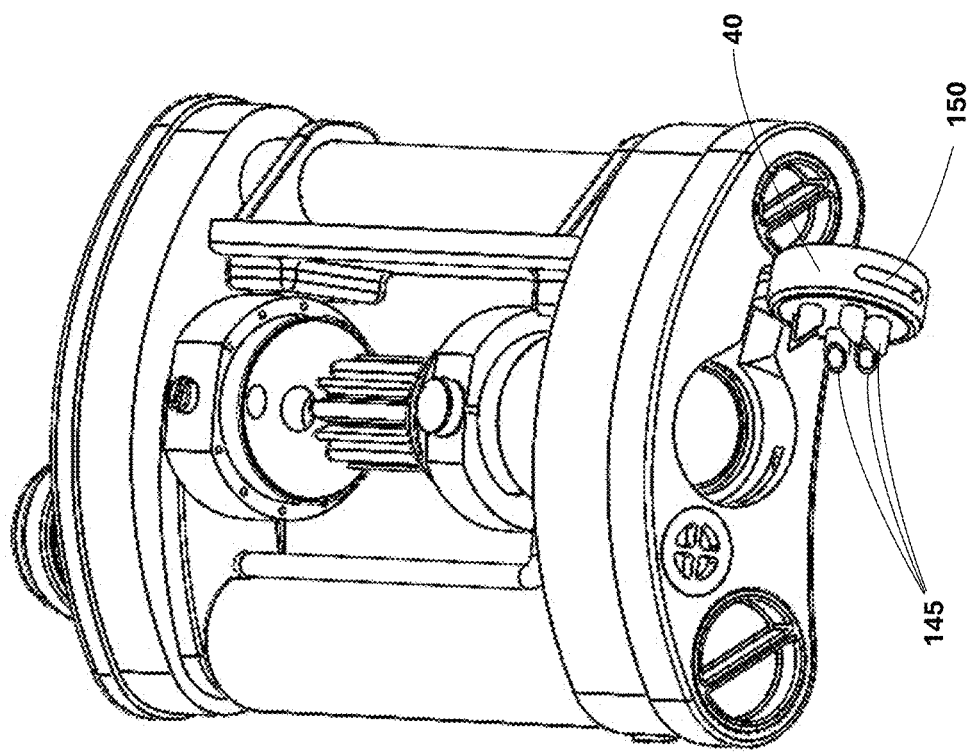
FIG. 3B, which is a perspective view of the vaporizing article of FIG. 1A, with the outer casing and window frames omitted, and with a container inserted therein.

The empty heat chamber 55 of the vaporizing article is best seen in FIG. 3A. FIG. 3B shows a similar view of the heat chamber but with a container 95 or 103 loaded therein. The heat chamber door 40 is provided with an air passageway 145 to allow the air to flow from outside the vaporizing article through the container 95 or 103. The air passageways in the exemplary embodiment are formed as puncture tubes that serve the secondary function of perforating the seal at the inlet of the container when the heat chamber door is closed by the user. To facilitate perforation of the container, the puncture tubes may terminate at an angle, as best shown in FIG. 3A. As will be described in greater detail below, when a user of the vaporizing article inhales from the mouthpiece 15, surrounding air is sucked into the vaporizing article through the one-way air intake valve 65 and flows through an opening 150 in the heat chamber door 40 and then through the puncture tubes 145 into and through the container 95 or 103 inside the heat chamber 55. Any commonly available one-way valves may be used for the one-way air intake valve provided it ensures that air or other vapour or gaseous mixture cannot escape the vaporizing article therefrom into the surroundings.

Additional components of the vaporizing article will now be described with reference to FIGS. 5A, 5B, 5C and 5D. The vaporizing article is provided with a cooling tower 155 and a flow tube 160 to permit the flow of fluid from the heat chamber 55 to the cooling tower 155. A vapour valve 165 is provided within the flow tube 160 at a point between the heat chamber 55 and the cooling tower 155. The portion of the flow tube 160 between the heat chamber 55 and the vapour valve 165 is referred to throughout the description as the holding chamber. The vapour valve 165 may be controlled by the user via the activation button 80. When the activation button 80 is in the resting state (i.e. it is not depressed), as is best illustrated in FIG. 5C, the vapour valve is in the bypass state, meaning that inhalation by the user causes surrounding air to enter the vaporizing article via the bypass air inlet 170. Such air is referred to throughout the description as bypass intake air. Bypass intake air enters the flow tube 160 downstream of the heat chamber (and holding chamber), therefore bypassing the gaseous by-products produced in the holding chamber as a result of the heating and/or combustion of the substance inside the heat chamber. A biasing element, such as a spring (not shown), may be used to bias the vapour valve in the bypass state (and therefore the activation button 80 in its resting state), as is generally known in the art.

When the activation button 80 is depressed by a user, the vapour valve 165 is caused to be in a state an activated state. When in the activated state, the vapour valve blocks the flow path to the bypass air inlet, and inhalation at the mouthpiece by the user causes surrounding air to enter the vaporizing article via one-way air intake valve 65, flow through the heat chamber 55, and through the flow tube 160 into the cooling tower 155. A vaporizing article with the activation button in the depressed state is illustrated in FIGS. 5B and 5D.

An example of a possible contemplated user interaction with the vaporizing article, and the fluid flow paths within of the vaporizing article will now be described in greater detail with reference to FIGS. 5A, 6, 7 and 8. The following described user interaction is included for illustrative purposes and the person of ordinary skill in the art would appreciate that variations of one or more of the user interaction steps may be varied and/or omitted without departing from the scope of this disclosure.

Figure 5A:
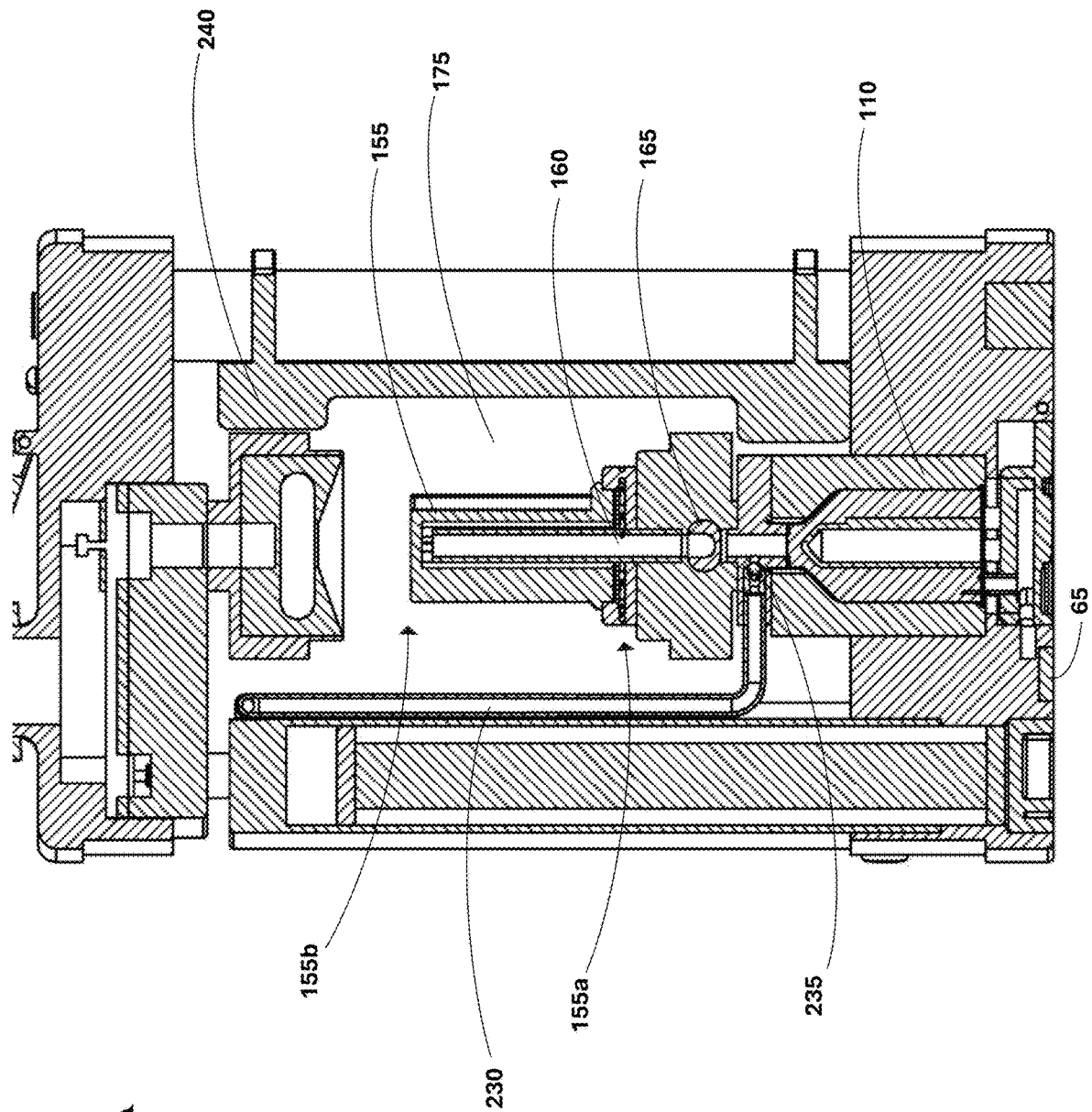
FIG. 5A, which is a front cross-sectional view of the vaporizing article of FIG. 1A.
Figure 5B:
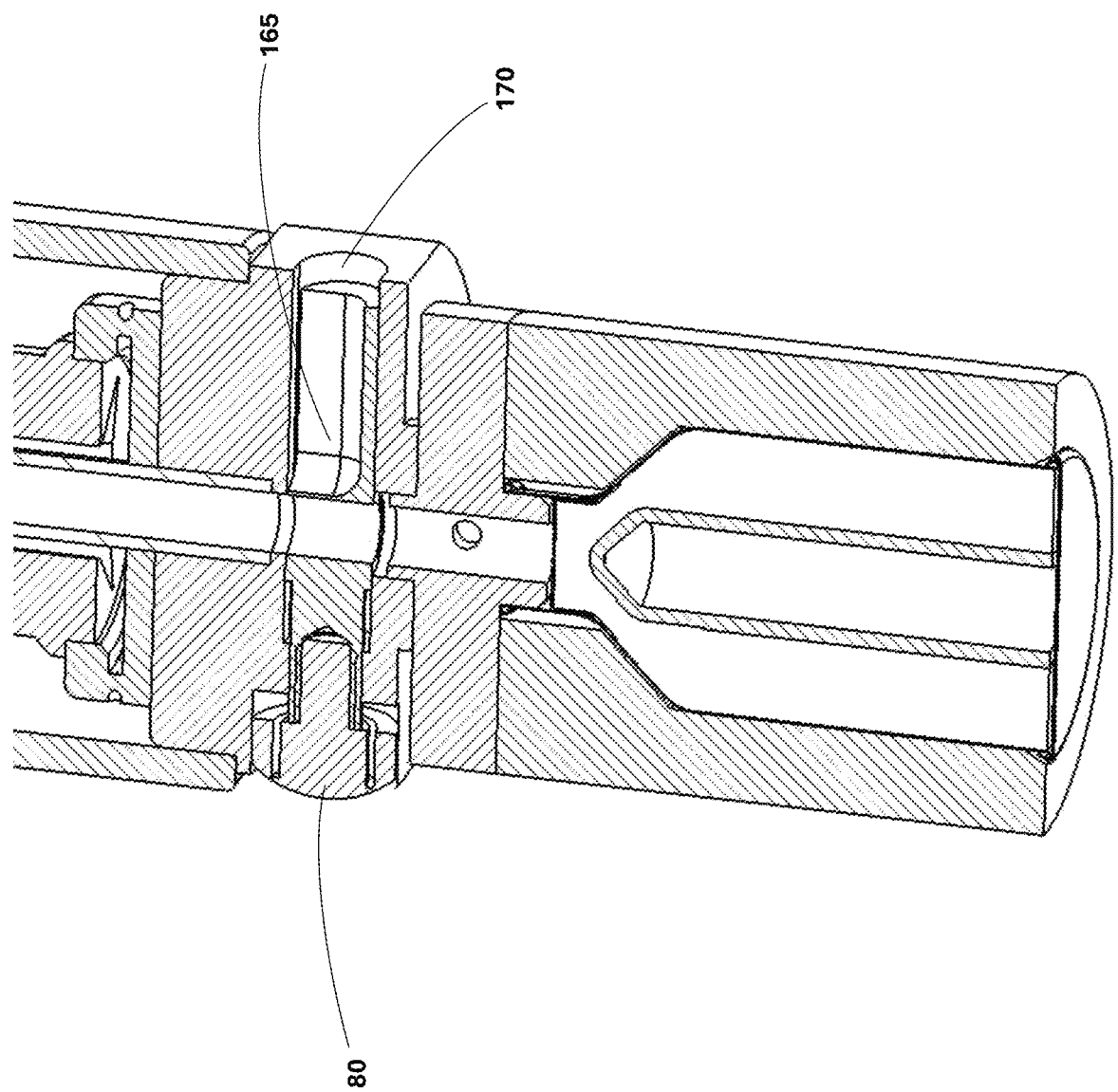
FIG. 5B, which is a cross-sectional view of the vaporizing article of FIG. 1A, enlarged to illustrate the vapour value mechanism.
Figure 5C:
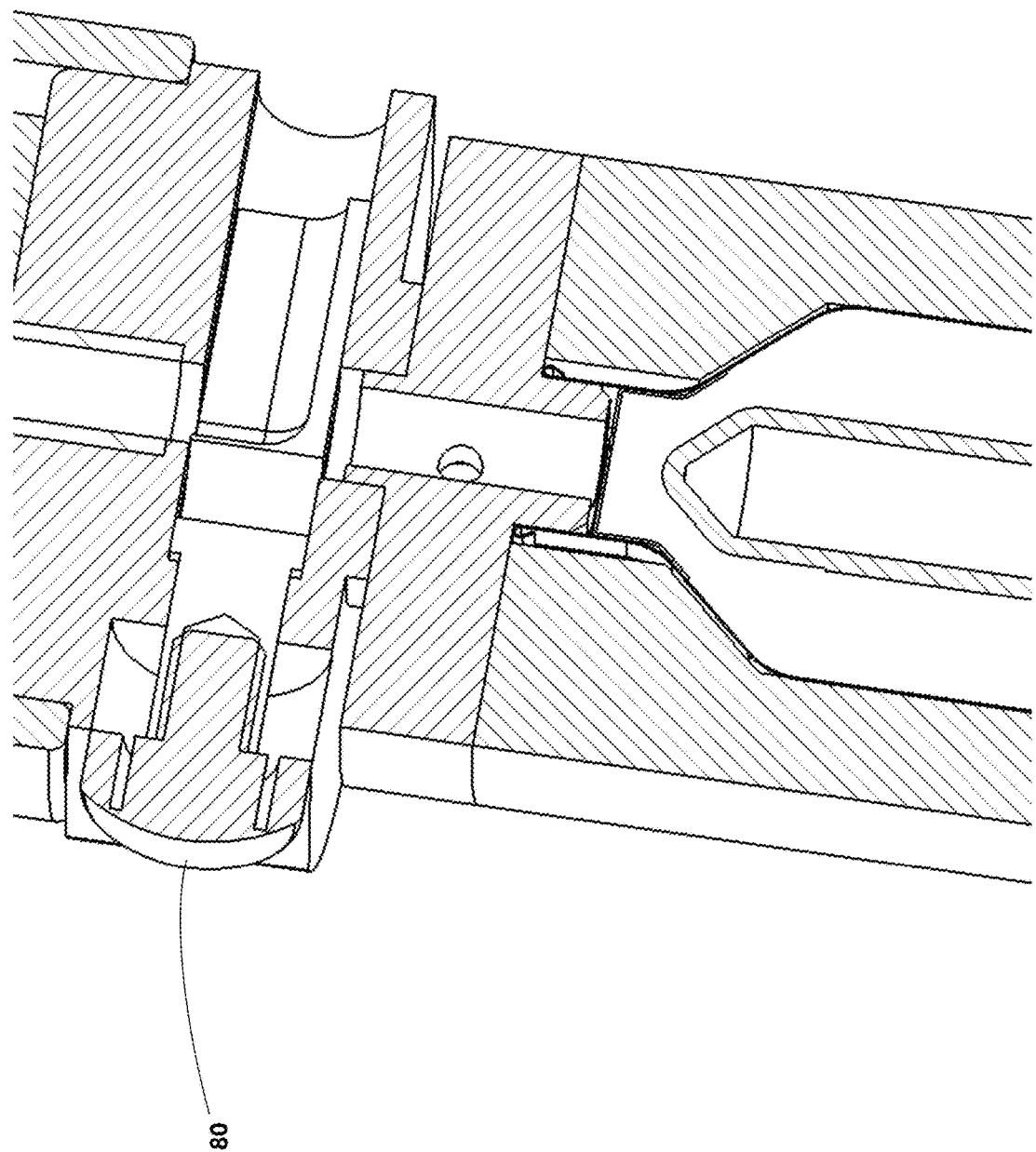
FIG. 5C, which is an enlarged view of the vaporizing article of FIG. 5B, illustrating the vapor valve in the bypass state.
Figure 5D:
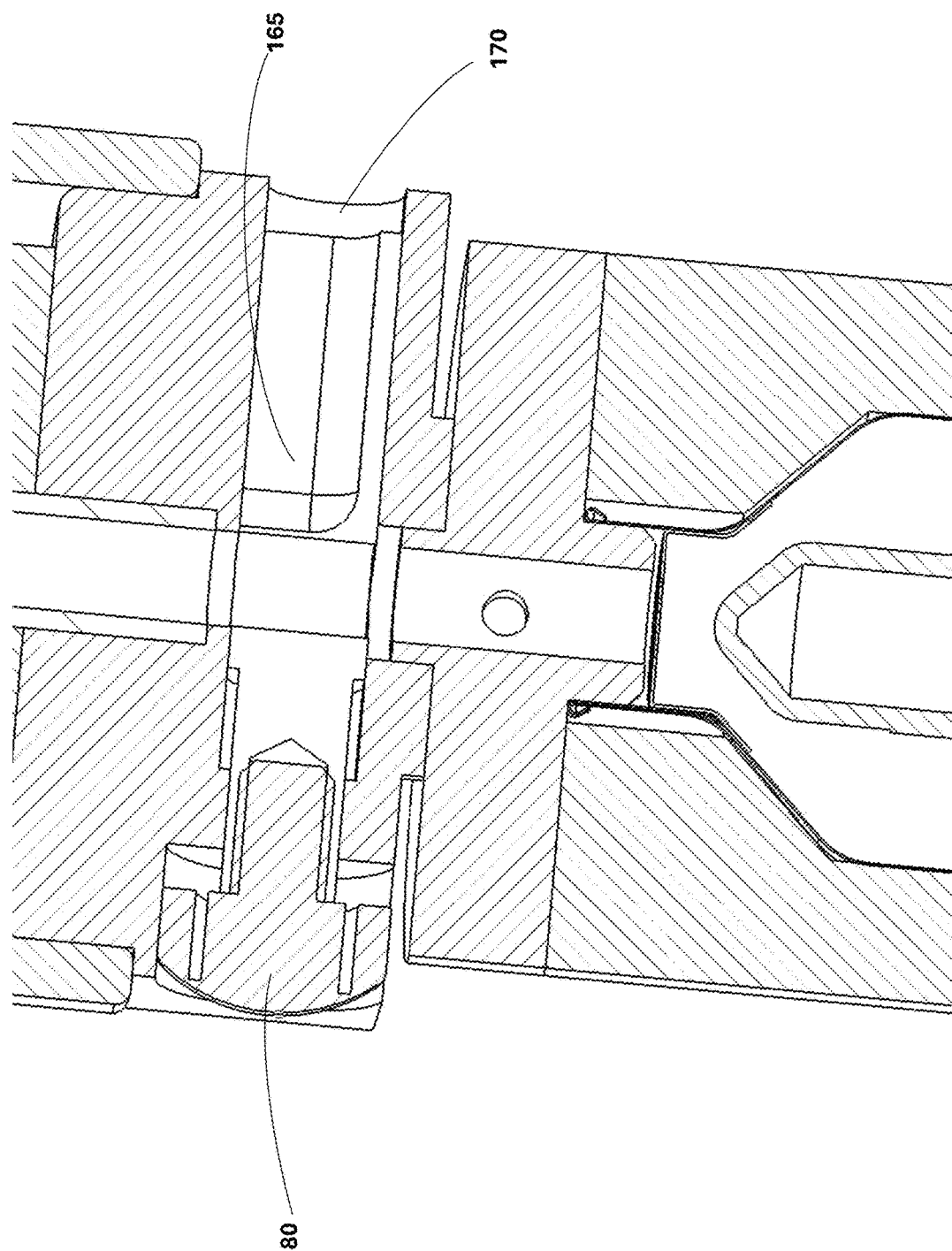
FIG. 5D, which is an enlarged view of the vaporizing article of FIG. 5B, illustrating the vapor valve in the activated state.

FIG. 5A shows a cutaway of a vaporizing article preloaded with a container containing the substance to be heated and/or combusted. The user may first turn on the vaporizing article by pressing and holding the power button. The LEDs 75 may be used to alert the user that the vaporizing article has been successfully turned on. The user may then press and release the power button to initiate heating of heat chamber 55.

The heat chamber may be heated using one or more heating elements 110 situated in close proximity to the heat chamber 55. Engagement of the heating elements would heat the contents of the heat chamber through conduction heating. Additionally, or in the alternative, a convection heating system may be incorporated into the vaporizing article which first heats air and then forces it through the heat chamber (from inlet to outlet) to heat its contents.

During the heating step, the activation button is in its resting state (i.e. not depressed), which obstructs the flow path between the heating chamber 55 and cooling chamber 175. The heat chamber may be heated using conventional heating methods known to those skilled in the art and may optionally utilize a PID loop control to allow the system to more accurately control the temperature possibly in accordance with user preferences. This includes a faster heat-up cycle with less temperature oscillations. The controls will allow the user to control the target temperature according to his or her preferences. The heating elements 110 may be configured to heat the heat chamber 55 to temperatures determined in accordance with generally known principles relating to the vaporizing and/or combustion of the substance being used. The heating causes vaporizing and/or combustion of the substance inside the heat chamber and traps the gaseous euphoric and/or medicinal by-products inside the vaporizing article upstream from the vapour valve 165. Once the heat chamber has reached the requisite level of heating, the user may be prompted, for example through the LEDs or a sound, that the smoke and/or vapour is ready to be inhaled.

Figure 6:
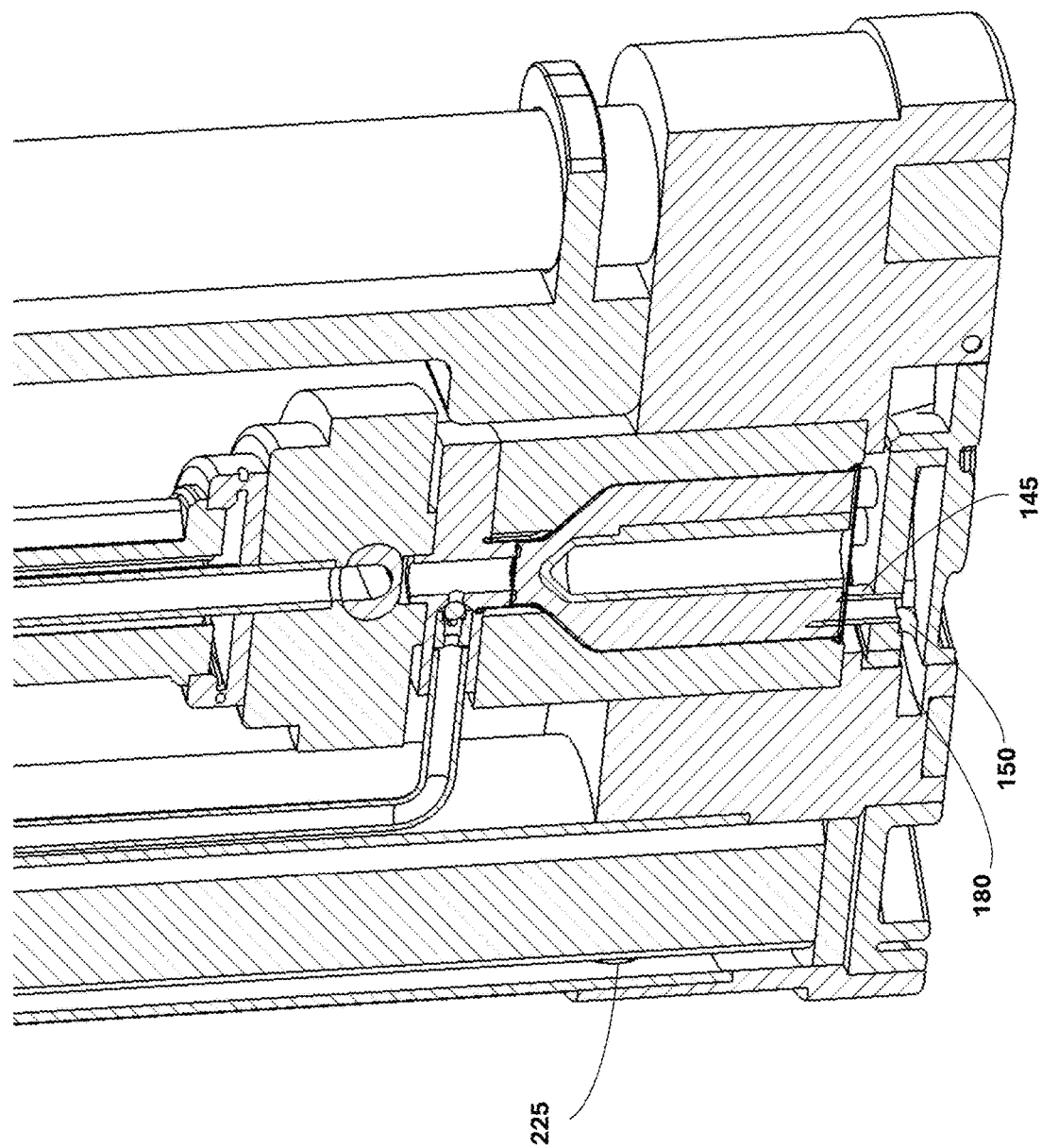
FIG. 6, which is a partial enlargement of the cross-sectional view of the vaporizing article of FIG. 5A.

When ready, the user may now press and hold the activation button 80 and inhale from the mouthpiece 15 to cause the gaseous substance by-product to travel toward the user's lungs. The flow of fluid through the vaporizing article from the one-way air intake valve 65 to the mouthpiece 15 will now be described with reference to FIGS. 6, 7 and 8. FIG. 6 is a partial enlargement of FIG. 5A and is provided to better illustrate fluid flow through the vaporizing article upstream of the cooling chamber. Inhalation with the activation button depressed causes surrounding intake air to enter the vaporizing article through one-way air intake valve 65, flow through intake air conduit 180, through the slot opening 150 in the heat chamber door 40, and then through the puncture tubes 145 into the container 95 or 103 within the heat chamber 55. The movement of intake air causes the gaseous by-products produced within the heating chamber to flow downstream into the cooling chamber 175.

Figure 7:
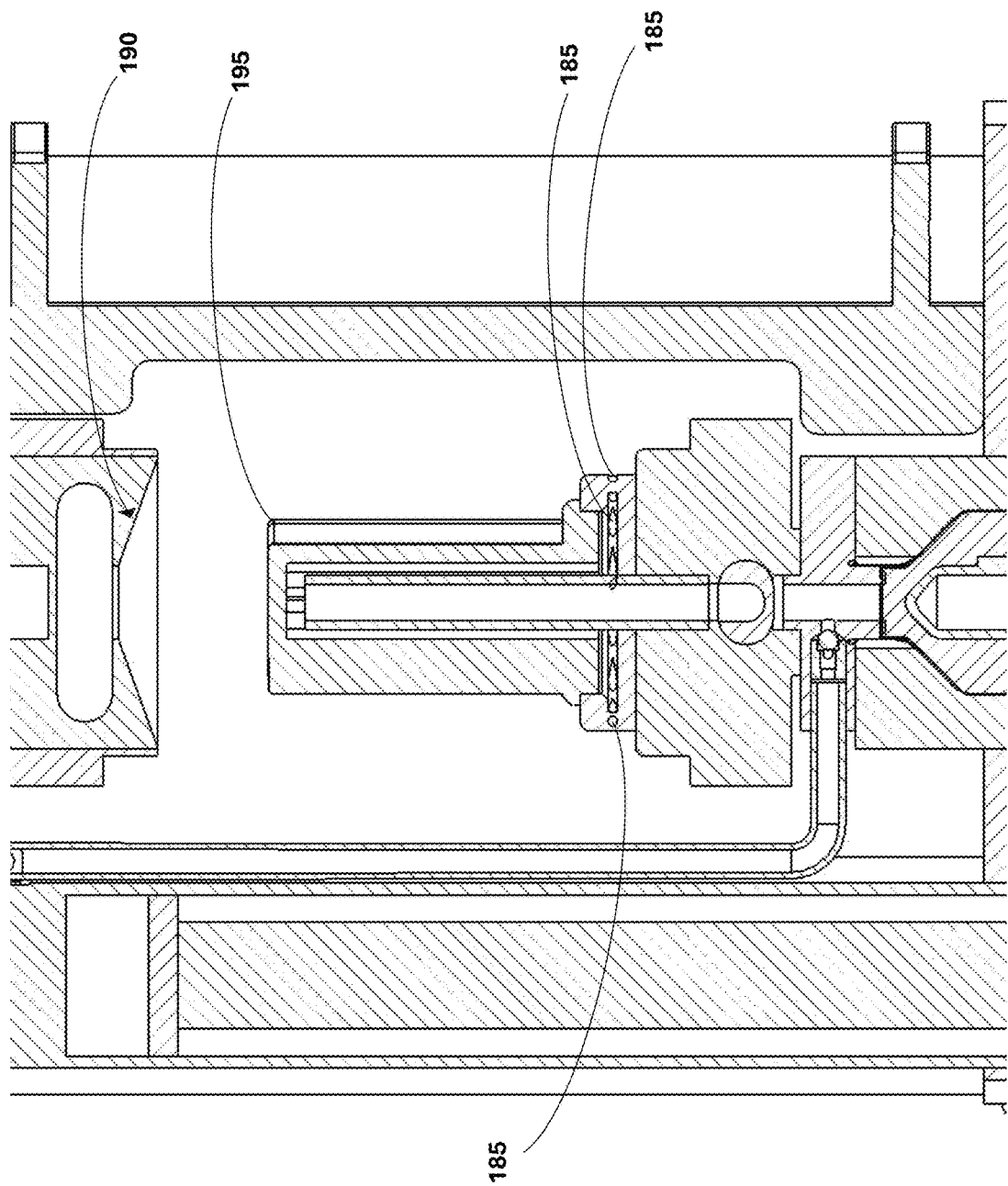
FIG. 7, which is a partial enlargement of the cross-sectional view of the vaporizing article of FIG. 5A.

FIG. 7 is a partial enlargement of FIG. 5A and is provided to better illustrate fluid flow through the vaporizing article downstream the heat chamber 55. The gaseous by-products enter the upstream end 155a of the cooling tower 155 through a flow tube 160 inside and concentric with the cooling tower 155 to the downstream end 155b of the cooling tower 155. The gaseous by-products then exit the flow tube 160 and are directed back toward the upstream end 155b and exit the cooling tower 155 through exit openings 185. The exit openings 185 may optionally be provided on an angle (as illustrated in FIG. 7) to provide a visible swirling-effect inside the cooling chamber. The cooling chamber may optionally be provided with water or another fluid to assist in both cooling and filtering the gaseous by-products prior to inhalation and to provide the user with a pleasing bubbling effect during inhalation. The user may add or remove water or other liquids into the cooling chamber via the liquid fill port 85. Once exited the cooling tower 155, the gaseous by-products flow toward the cooling chamber exit 190. The outside of the cooling tower 155 may be configured to enhance its ability to cool the gaseous by-products as they flow toward the cooling chamber exit 190. For example, the cooling tower in the illustrated exemplary embodiment is provided with fins 195 (best shown in FIG. 1E) to maximize the surface area of the cooling tower that the gaseous by-products contact on the inside, and that the liquid contacts on the outside.

Figure 8A:
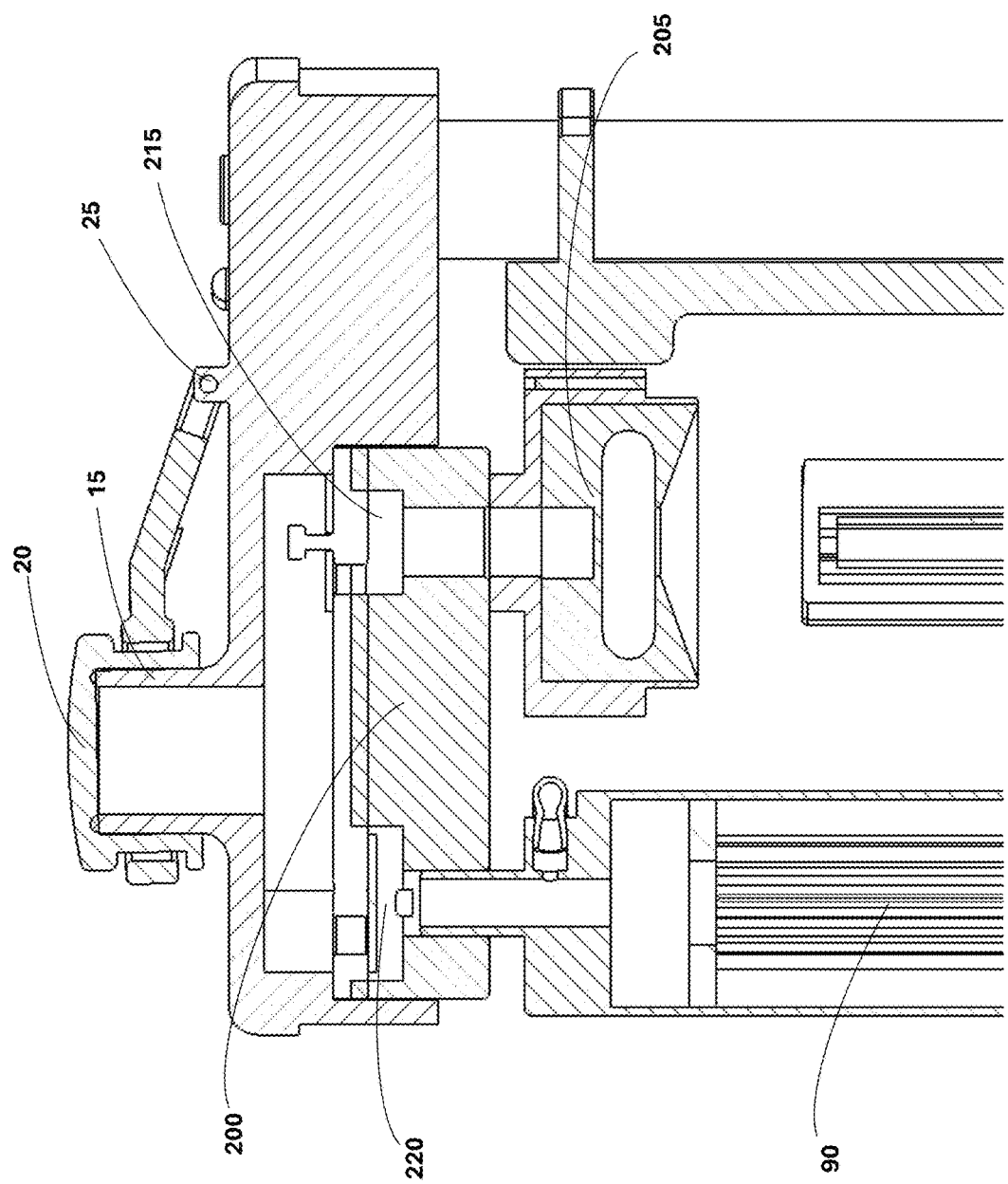
FIG. 8A, which is a partial enlargement of the cross-sectional view of the vaporizing article of FIG. 5A; and, FIG. 8B, which is perspective cut-away view of the vaporizing article of FIG. 5A, better illustrating the bypass conduit.
Figure 8B:
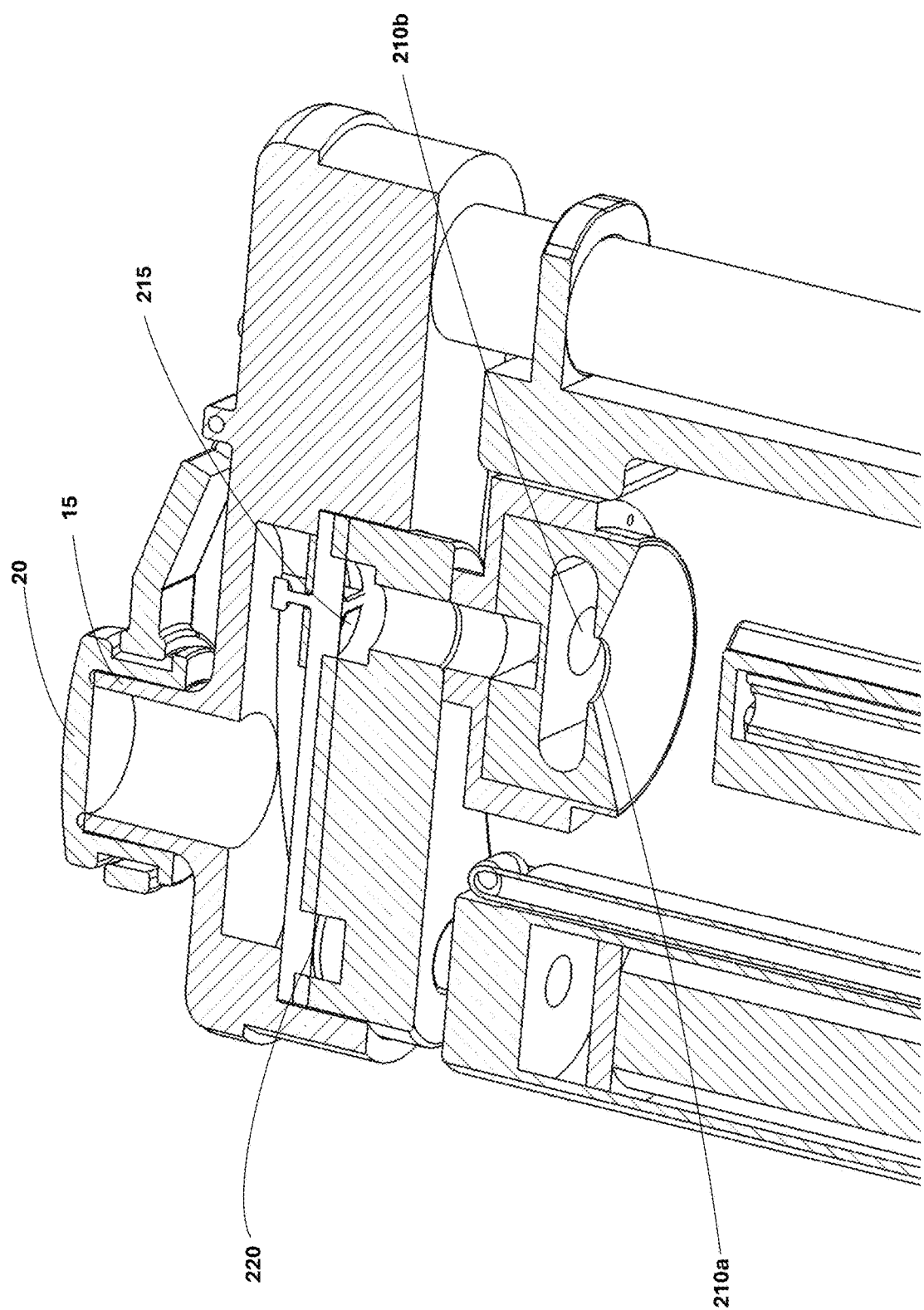

FIGS. 8A and 8B show a partial enlargement of the vaporizing article of FIG. 5A and are provided to better illustrate fluid flow downstream of the cooling tower 155. Fluid exiting downstream of the cooling tower 155 is directed toward an inhale/exhale manifold 200. In the described exemplary embodiment, an optional splash protector piece 205 has been provided between the cooling tower 155 and the inhale/exhale manifold 200. The splash protector 205 may be desirable where the vaporizing article is being used with liquid inside the cooling chamber 175 and helps to prevent the liquid from travelling from the cooling tower 155 into the user's mouth. Splash guard 205 requires the liquid flowing from the cooling tower to pass through a set of offset openings 210a, 210b, which permit gaseous (i.e. vapour) flow through the splash protector 205 while restricting the through-flow of liquid.

The gaseous by-products then flow into the inhale/exhale manifold 200 through the manifold inlet valve 215 and out through the mouthpiece 15 toward the user's lungs. Inhalation by the user causes closure of the manifold exhale valve 220, thereby ensuring that the user is not inhaling air from the filter chamber 60. Once the user has inhaled the desired amount of gaseous by-products, he or she may release the activation button and continue to inhale from the vaporizing article for a period of time. Releasing the activation button causes the vaporizing article to be in the idle state. In the idle state, the vapour valve is in its resting position and surrounding air is caused to enter the vaporizing article through the bypass air inlet 170 (FIG. 5B). Inhaling through the mouthpiece 15 while the vaporizing article is in idle state causes a flow of surrounding air (i.e. air without gaseous by-products, or clean air) toward the user's lungs. Inhaling additional clean air helps to ensure that all of the gaseous by-products the user has inhaled from the vaporizing article reach the user's lungs for maximum euphoric and/or medicinal effects. The additional inhalation from the vaporizing article when in the idle state also causes a purging of the vapour within the vaporizing article downstream of the vapour valve, which helps to prevent gaseous by-products lingering and getting stale inside the vaporizing article between inhalations. The vapour valve may be positioned upstream from the cooling chamber 175 and as close to the heat chamber 55 as possible to allowing purging of as much of the vaporizing article as possible.

Optionally, the vaporizing article may provide the user with the ability to preset the amount of gaseous by-product to be inhaled as well as the amount of bypass air to be subsequently inhaled. This level of control may be achieved by the user using a dial, digital display, timer with visual/audible indicator, or handheld device such as a smart phone using wireless technology (e.g. Bluetooth), which would cause the article to electronically control the vapour valve in accordance with the user's input settings. This would provide the user with a consistent experience with each inhalation and could also eliminate the need for the user to mechanically control the vapour valve.

The user may also optionally be provided with a concentration control mechanism to allow the ability to set a desired ratio of gaseous by-products to bypass air to be inhaled should the user desire to control the concentration of gaseous by-products being inhaled. Users that are more sensitive to the euphoric or medicinal effects of the gaseous by-products or have a sensitive throat or lungs may wish to inhale at a lesser concentration. Conversely, other users may wish to inhale at a higher concentration to maximize the euphoric or medicinal effects. The concentration control mechanism would allow the user to experiment with different concentrations and settle on the concentration that best suits his or her preferences. The user may control the concentration through, for example, a dial, digital display, or wireless technology (e.g. Bluetooth) using a smart phone.

Once the user is ready to exhale, he or she may do so back into the device, for example, via mouthpiece 15. Although it may be preferable to allow the user to inhale and exhale using a single mouthpiece, the user may alternatively be provided with a separate mouthpiece for exhaling. Exhaling into the mouthpiece 15 causes the manifold inlet valve 215 to close and the manifold outlet valve 220 to open, causing the exhaled fluid to flow through the filter chamber 60. The filter 90 inside the filter chamber 60 filters the exhaled fluid before it exits the vaporizing article at the filter chamber outlet port 225 (FIG. 1D), such that the exhale fluid re-entering the surroundings is substantially free of contaminant.

With returning reference to FIG. 5A, a pressure-relieving bypass conduit 230 may be provided to provide a fluid flow path between a point along the fluid flow path between the heat chamber 55 and the cooling chamber 175, and the filter chamber 60. The bypass conduit 230 is provided with a one-way check valve 235 that restricts fluid flow between the holding chamber and the filter chamber 60. The check valve 235 is configured to only allow flow from the holding chamber to the filter chamber 60 and to open only once a pre-determined pressure is reached within the holding chamber. In this way, if the holding chamber reaches a high enough pressure, due for example to over heating of the substance, the pressurized fluid within the holding chamber is permitted to escape through the bypass conduit 235 into the filter chamber 60 to be filtered prior to being released into the surroundings. The bypass conduit 235 therefore also allows for the filtration of gaseous by-products while the article is idle between inhalations.

The device may be controlled via electronic circuitry. This may include a circuit board with a microprocessor and Bluetooth capabilities. The microprocessor would process a number of inputs and control a number of outputs. The inputs would include the on/off and settings button, inputs via Bluetooth connectivity to a smart phone, inputs from the activation button and from various sensors, including a temperature sensor. The outputs may include various indicator lights, glass tube lighting, the heating element, etc. The microprocessor would contain basic programming to accommodate PID loop temperature control, safety functions e.g. prevent overheating, battery status and vaporization optimization coding, to allow the system to more effectively manage vaporization during idle periods, in between inhalations. For example, the heater will drop to a lower temperature to minimize vaporization in between inhalations. The electronic circuitry may be contained, for example, on a PCB 240, secured within the vaporizing article.

The vaporizing article may also provide the user with the ability to control the temperature to which the heat chamber is heated, allowing the tobacco or *Cannabis* to be vaporized or burnt at multiple settings, resulting in various vapour or smoke outputs. Typical burning temperatures range from 200° C. to 240° C., but temperature settings may not necessarily be limited to those within that temperature range. If desired, the user may pre-set the temperature for the heat chamber and have it held constant throughout the use of the article. The user may control the heating temperature through, for example, a dial, digital display, or wireless technology (e.g. Bluetooth) using a smart phone.

Many modifications of the embodiments described herein as well as other embodiments may be evident to a person skilled in the art having the benefit of the teachings presented in the foregoing description and associated drawings. It is understood that these modifications and additional embodiments are captured within the scope of the contemplated disclosure which is not to be limited to the specific embodiments disclosed.

What is claimed is:

1. A vaporizing article comprising:
    a heating chamber for receiving a substance to be heated;
    heating means for inducing a gaseous by-product from the substance;
    a mouthpiece to allow inhalation of the gaseous by-product by a user and accept exhaled air from the user;
    filtering means for decontaminating the exhaled air prior to its dissipation into the surroundings; and
    a heat chamber door to permit selective access to the heat chamber to facilitate the introduction of substance into the heating chamber,
    wherein the heat chamber door comprises an air passageway to allow air outside of the vaporizing article to be drawn into the heating chamber and
    wherein the heat chamber door comprises protrusions configured to pierce a sealed container of substance inside the heating chamber when the heating chamber door is closed.

2. A container for use in a vaporizing article, the container for holding a substance which when heated produces a gaseous by-product for inhalation by a user of the vaporizing article, the container comprising:
    a substantially cylindrical shaped exterior body spanning a first end and a second end of the container, the second end being substantially nozzle-shaped;
    a central core positioned within the body and extending from the first end of the container toward the second end of the container; and,
    one or more thermally conductive spokes connecting the exterior wall to the central core,
    wherein heat applied to the container causes heat to be transferred to the substance by walls of both the exterior body and the central core.

3. The container of claim 2 further comprising an airtight perforable sealing enclosure at the first end and a removable cap at the second end.

4. The container of claim 2 wherein the central core is void of substance.

* * * * *